United States Patent
Schersl

(10) Patent No.: US 6,465,665 B1
(45) Date of Patent: Oct. 15, 2002

(54) HIGH EFFICIENCY PROCESS FOR THE RECOVERY OF THE HIGH PURE STEROLS

(75) Inventor: Endre Markovits Schersl, Quilpué (CL)

(73) Assignee: Thomas Francis Harting Glade, Santiago (CL)

( * ) Notice: Subject to any disclaimer, the term of this patent is extended or adjusted under 35 U.S.C. 154(b) by 0 days.

(21) Appl. No.: 09/654,410

(22) Filed: Sep. 1, 2000

(30) Foreign Application Priority Data

Sep. 3, 1999 (CL) .............................................. 2026/99

(51) Int. Cl.⁷ .............................. C07J 9/00; B01D 3/00
(52) U.S. Cl. ........................... 552/545; 203/60; 203/63
(58) Field of Search .......................... 552/545; 203/60, 203/63

(56) References Cited

U.S. PATENT DOCUMENTS

| | | | |
|---|---|---|---|
| 2,591,885 A | * 4/1952 | Smith | 260/97.7 |
| 2,716,630 A | * 8/1955 | Spangenberg et al. | 202/52 |
| 2,866,739 A | 12/1958 | Ciesielski et al. | |
| 3,031,376 A | 4/1962 | Levin et al. | |
| 4,076,700 A | 2/1978 | Harada et al. | |
| 4,151,160 A | 4/1979 | Koebner | |
| 4,298,539 A | * 11/1981 | Koskenniska | 260/397.25 |
| 4,422,966 A | 12/1983 | Amer | |
| 4,524,024 A | * 6/1985 | Hughes | 260/97.6 |
| 4,524,030 A | 6/1985 | Cleary et al. | |
| 4,874,794 A | 10/1989 | Katz | |
| 5,071,879 A | 12/1991 | Katz | |
| 5,117,016 A | * 5/1992 | Tackett et al. | 552/545 |
| 5,166,219 A | 11/1992 | Katz | |
| 5,244,887 A | 9/1993 | Straub | |
| 5,270,041 A | 12/1993 | Eugster et al. | |
| 5,502,887 A | 4/1996 | Gonzales | |
| 5,534,554 A | 7/1996 | Katz et al. | |
| 6,057,462 A | * 5/2000 | Robinson et al. | 552/545 |

FOREIGN PATENT DOCUMENTS

WO        00/64924        11/2000

OTHER PUBLICATIONS

Ault, Techniques and Experiments for Organic Chemistry, 2nd edition, 1976.*

Ault, A., "Techniques and Experiments for Ogranic Chemistry," 2$^{nd}$ Ed. pp. 29–41 (1976).

* cited by examiner

Primary Examiner—Barbara P. Badio
(74) Attorney, Agent, or Firm—Baker & McKenzie

(57) ABSTRACT

A high efficiency continuous process for the recovering high purity sterol mixtures from mixtures of neutral compounds obtained form black liquor soap skimings of the cellulose pulping industry or from tall oil pitch comprising the steps of distillation, crystallization and recirculation of the mother liquor residue.

17 Claims, 2 Drawing Sheets

HIGH EFFICIENCY PROCESS FOR THE RECOVERY OF THE HIGH PURE STEROLS

FIELD OF THE INVENTION

The present invention relates to a continuous process of high yield for recovering high purity sterol mixtures from mixtures of neutral compounds obtained form black liquor soap skimings of the cellulose pulping industry or from tall oil pitch.

BACKGROUND OF THE INVENTION

Black-liquor soaps are by-products of the Kraft pulping process of pine and other woods. Typically, during the Kraft process, wood chips are digested for two hours at 170° C. in an aqueous liquor containing sodium hydroxide and sodium sulfide. The digestion delignifies wood and produces a dark aqueous suspension called black liquor, which along with lignin contains cellulose pulp, rosin and fatty acid sodium soaps, a series of neutral organic products such as sterols, diterpenes, fatty alcohols, stilbenes, sterol and fatty alcohol esters and products resulting from lignin degradation. Under these conditions, the cellulose is stable and remains in suspension in the black liquor. When digestion is finished, the cellulose pulp is separated from the black liquor and washed. The pulp can be used as such or subjected to later purification processes.

Black liquor must be recovered for both economic and environmental reasons. To this end, the liquor is concentrated by evaporation to a concentration of about 23–32% in weight of black liquor solids. From said black liquor solids, fatty acid and rosin acid soaps are separated along with a series of hydrophobic or neutral matter suspended in these soaps and concentrated on the top of the container where they are removed or skimmed off. In technical literature, this fraction is called "skimmings". Other terms used for the same fraction are "tall oil soap" or "CSS" (Crude Sulfate Soap) or "BLSS" (Black Liquor Soap Skimmings).

Generally the skimmings contain between 30 and 50% of water. The solid matter is a complex mixture of rosin acid and fatty acid sodium soaps and a series of hydrophobic compounds comprising sterols, stanols, fatty alcohols, diterpenes, stilbenes and non-saponified sterol esters, stanol esters and fatty alcohol esters, which together may constitute up to 25% of the skimmings solids. The neutral matter of black liquor soaps can be separated from the rosin acid and fatty acid soaps by means of solvent extraction processes known in the state of art, and also by means of molecular distillation as disclosed in Chilean Patent Application 873/98.

The mixture of neutral compounds obtained from black liquor soap usually also contains varying amounts of esters of sterols and esters of long chain aliphatic alcohols or fatty alcohols not saponified during the pulping process. When the mixture of neutral compounds is fully saponified and the soaps formed are separated from the saponified mixture, a mixture of unsaponifiable material is obtained. Another source of neutral matter is tall oil pitch. In this invention, the terms "mixture of neutral matter" or "neutral matter" means a mixture comprising unsaponifiable matter which might also comprise unsaponified saponifiable matter, typically esters of sterols or stanols and esters of fatty alcohols.

A typical composition of the unsaponifiable material obtained from black liquor soap by means of solvent extraction processes is as follows: Monoterpenes (α-terpineol) 0.3%; Diterpenes (about 45 parts) 41.2%; Steroids (about 17 parts) 32.4%; Triterpenes (about five parts) 0.6%; Polyprenols 0.7% Wax alcohols (about ten constituents ) 6.1%; Stilbenes (about two parts) 5.7%; Lubricating oil 4.4% and minor parts 8.6%. Unsaponifiable matter obtained from saponified tall oil pitch usually contain the same components although in different proportions; in general, it contains less fatty alcohols. The composition of tall oil pitch is strongly dependent on the distillation equipment and operating conditions employed in the distillation of tall oil.

Skimmings may be used as fuel oil; its calorific value is a little lower than the half of fuel oil calorific value. It may also be transformed into tall oil by adding sulfuric acid and separating the oil from the aqueous phase. This oil is known as CTO (crude tall oil). Then, CTO is exposed to a series of vacuum distillations producing fatty acids (TOFA or tall oil fatty acids), which constitute one of the most valuable fractions of CTO; rosin acids (TORA or tall oil rosin acids); distillate tall oil (DTO), which has many uses; and pitch, the bottom of the distillation, which is used as fuel or as an ingredient for the preparation of asphaltic emulsions. Lately, the pitch has been considered as a convenient source of sterols because it contains between 7–20% of sterols either free or in esterified form.

The following are processes disclosed for obtaining sterols from neutral matter of black liquor soap skimmings or from tall oil pitch:

U.S. Pat. No. 2,499,430 to Christenson and Vogel teaches a liquid-liquid extraction process to recover sterols from saponified tall oil.

U.S. Pat. No. 2,528,025 to Whyte teaches a process for the isolating of sterols by means of crystallization from methyl cyanide solutions.

U.S. Pat. No. 2,530,809 teaches the crystallization of sterols from a solution of a lower alcohol or acetone.

U.S. Pat. No. 2,536,753 to Knol teaches the recovery of sterols by means of the formation of addition compounds with zinc chloride and then decomposing said compounds.

U.S. Pat. No. 2,568,202 to Hackmann and Overhoff teaches the process of recovery of sterols by forming addition products of sterols with metal salts under anhydrous conditions.

U.S. Pat. No. 2,573,265 to Folzenlagen and Lange teaches a process for separating sterols from unsaponifiable material, by means of first forming a solution in an oxygen-free liquid solvent then precipitating sterols with perchloric acid.

U.S. Pat. No. 2,573,891 to Christenson teaches the dissolution of a sterol concentrate and its partition in immiscible mixture of solvents followed by the recovery of a refinate rich in sterols.

U.S. Pat. No. 2,585,954 to Mattikov and Perlman teaches the recovering of sterols from phosphatidic material by a combined solvent extraction and crystallization process.

U.S. Pat. No. 2,697,503 to Christenson teaches a process of obtaining a concentrate of unsaponifiable matter of soybean oil and the obtainment of sterols thereof by means of solvent extraction followed by evaporation.

U.S. Pat. No. 2,715,639 to Albrecht and Herrlinger teaches the recovery of sterols from tall oil pitch by first saponifying said pitch, diluting with warm water and then cooling to precipitate sterols.

U.S. Pat. No. 2,729,656 to Berry and Miller teaches a process of recovering sterols by saponifying the sterol containing material, separating soaps and sterols with an solvent followed by crystallization.

U.S. Pat. No. 2,729,655 to Cunningham and Greiner teaches a process of recovering sterols by acidifying a saponification reaction mixture, esterifying fatty acids and recovering sterols from the esterification mixture.

U.S. Pat. No. 2,866,797 to Berry et al. teaches an improved process of isolating sterols from a solution of ethylene dichloride to which water and methanol is added to precipitate sterols.

U.S. Pat. No. 3,108,120 to Brown and Meng teaches the recovery of sterols and tocopherols from unsaponifiable matter by extracting with a selective solvent.

U.S. Pat. No. 3,691,211 to Julian teaches a process for preparing sterols from plant sources, especially tall oil pitch, by extraction in a water-alcohol-hydrocarbon mixture followed by saponification and subsequent recrystallization and leaching.

U.S. Pat. No. 4,044,031 to Johansson et al. teaches a process for the separation of sterols from mixtures of unsaponifiables obtained from crude soap skimming by extraction of a suitable solvent followed by crystallyzation.

U.S. Pat. No. 4,076,700 to Harada and Yamamoto teaches a process of recovering sterols from tall oil skimming soap by first dehydrating the mixture and evaporating from said mixture sterols in a thin film evaporator.

U.S. Pat. No. 4,153,622 to Koskenniska teaches the recovery of sterol from unsaponifiables obtained from crude soap skimming by dissolving in acetone, filtering with active carbon, concentrating and cooling to crystallize sterols.

U.S. Pat. No. 4,265,824 to Koskenniska teaches a process for the isolation and recovery of beta-sitosterol from the unsaponifiables obtained from crude soap skimming by treating with an acid in an organic solvent, then cooling and filtering to yield beta-sitosterol.

U.S. Pat. No. 4,298,539 to Koskenniska teaches a process for the isolation of beta-sitosterol from the unsaponifiables obtained from crude soap skimming by treating with solvent mixture containing aromatic hydrocarbon, polar solvent, and water; dissolving, precipitation.

U.S. Pat. No. 4,420,427 to Hamunen teaches a process for the separation of sterols or mixtures of sterols from the neutral substance of crude soap from sulphate cellulose process by means of extracting with a suitable solvent, cooling to crystallize, filtering and washing the precipitate.

U.S. Pat. No. 4,422,974 to Hamunen teaches a process for the purification of beta sitosterol isolated from the unsaponifiables in crude soap from sulphate cellulose process by crystallization from organic solvent-water mixture.

U.S. Pat. No. 4,524,024 to Hughes teaches a process of recovering fatty acids and sterols from tall oil pitch by dissolving said pitch in a solvent, and separating sterols and high molecular weight alcohols together by a liquid-liquid extraction process.

U.S. Pat. No. 4,882,065 to Border teaches an adsorptive separation process for sterols from tall oil.

U.S. Pat. No. 4,977,243 to Border et al. teaches an adsorptive separation process for separation of sterols from a feed mixture.

Chilean Patent Application No. 85/98 teaches a process for the recovering of sterols and fatty alcohols from the unsaponifiables obtained from crude soap skimming by means of a molecular distillation process.

Chilean Patent Application 873/98 teaches a process for the recovery of sterol and other components from crude soap skimming or from neutralized tall oil by using short path distillation.

In general, the prior art processes, which are mainly addressed to the recovery of sterols from unsaponifiable matter obtained from black liquor soap skimmings or from saponified tall oil pitch are capable of either recovering high purity sterols with unsatisfactory to fair yields (80% or less) as of the crystallization methods, or recovering sterols in high yield but only with unsatisfactory to fair purity (90% or less) as of the molecular distillation processes taught in Chilean Patent Applications quoted above. The process hereby invented addresses satisfactorily both requirements; it has a very high yield, using mixtures of neutral matter comprising both unsaponifiable and saponifiable matter also, and the purity of the recovered sterols is also higher than those obtained by any known process in the state of art. All these features of the invented process constitutes the improvement over the prior art.

SUMMARY OF THE INVENTION

The objective of the present invention is to provide a continuous process of high yield for the recovery sterols or mixture of sterols of high purity, from mixture of neutral matter obtained from black liquor soap skimmings or tall oil pitch herein after referred to as "pitch."

It has been found that a conventional distillation of a mixture of neutral matter in a rectifying column, followed by distilling the heavy bottom condensate from said column in a short path distillation column so as to obtain a sterol concentrate, and then crystallizing said sterol concentrate in a mixture comprising a liquid hydrocarbon solvent, short chain aliphatic alcohol and water, followed by the steps of separating the mother liquor and evaporating the solvents of said mother liquor, give rise to a residue whose sterol content is substantially the same or even higher than the sterol content of the mixture of neutral matter that is fed to the rectifying column. This unexpected finding allows the feeding back or recirculating of the residue of the mother liquor to the rectifying column, without affecting the sterol content of the feed so as to allow for the continuous recovery of sterols of high purity, with an overall yield over 90%. Were not for said unexpected finding, the only way to increase yield would have been to resort to multiple crystallization steps, leading to unavoidable losses in each further step, thus preventing high yield recovery of sterols.

Likewise it has been found that by reversing the order of the distillation by first distilling the mixture of neutral matter in a short path distillation column followed by distilling the light condensate from the column in a rectifying column so as to obtain a sterol concentrate and then crystallizing said sterol concentrate in a mixture comprising a liquid hydrocarbon solvent, short chain aliphatic alcohol and water, followed by the steps of separating the mother liquor and evaporating the solvents of said mother liquor, give rise to a residue whose sterol content is substantially the same or higher than the sterol content of the mixture of neutral matter that is fed to the short path distillation column. This unexpected finding allows the feeding back or recirculating the residue of the mother liquor to the distillation system, without affecting the sterol content of the feed so as to allow for the continues recovery of sterols of high purity, with an overall yield over 90%. Were it not for said unexpected finding, the only way to increase yield would have been to resort to multiple crystallization steps, leading to unavoidable losses in each further step, thus preventing the recovery of sterols with high yield.

DETAILED DESCRIPTION OF THE INVENTION

Raw Materials

The raw material used in the disclosed process is composed by a mixture the neutral matter obtained from black liquor soap skimmings from local cellulose industries, although the raw material can also be mixtures of neutral matter of any origin. Likewise, the raw material may be constituted by the neutral matter obtained from tall oil pitch.

Mixture of neutral matter can be extracted by procedures known in the state of the art. When said mixture of neutral matter is extracted with organic solvents, said extracted mixture of neutral matter have to be first subjected to a solvent removal step. This step can be effected by applying heat at normal pressure or, preferably, at reduced pressure.

Raw materials of the present invention can also be composed by solvent-free mixture of neutral matter mixed with one or more fractions obtained from the process herein disclosed, or by solvent-free mixture of neutral matter mixed with any product comprising constituents of said mixture of neutral matter. Thus, for instance, esters of the mixtures of neutral matter, once separated from said mixture of neutral matter can be hydrolyzed and this hydrolisate can be mixed with the mixture of neutral matter.

Description of the Process

For the purpose of this invention, the raw material of the invention can conveniently be divided into three fractions: a fraction called wax, comprising long chain fatty alcohols; a fraction called sterol concentrate, comprising a mixture of free stanols and sterols; and a third fraction called esters comprising esters of fatty alcohols and esters of sterol or stanols.

The first objective of the present invention is to provide a process to produce a highly pure sterol concentrate with high yield from the raw material. Said process comprising the steps of:

(1) Distilling the raw material in a first distillation system comprising a packed bed or perforated plate rectifying column, a condenser and a reboiler comprising either a thin film evaporator or a falling film evaporator. To this end, the raw material, which is solid at room temperature, is heated until it liquefies and in this condition it is fed to the first distillation system. The pressure on the top of the rectifying column is higher than or equal to 0.1 mbar, preferably lower than 50 mbar, and the reboiler pressure is higher than or equal to 1 mbar, preferably lower than 100 mbar, depending on the number of theoretical stages or the number of equivalent theoretical height of the column. The temperature of the reboiler or heated surface of the thin film evaporator or the falling film evaporator is higher than or equal to 100° C., preferably lower than 400° C. From said first distillation system a distillate denoted as light overhead condensate comprising mainly wax, and a raffinate denoted as heavy bottom condensate comprising mainly a mixture of sterol concentrate and esters are recovered;

(2) Feeding the heavy bottom condensate of step (1) to a second distillation system comprising a short path distillation column comprising a heated and an internal condenser close to the heated surface. The temperature of the heated surface of said column is higher than or equal to 100° C., preferably lower than 400° C. and the pressure in said column is higher than or equal to 0.001 mbar, preferably lower than 25 mbar. The temperature of the internal condenser surface is lower than the temperature of the heated surface. Under these operating conditions, the feed of the second distillation system is efficiently fractionated into a light condensate, condensing and flowing down at the internal condenser, comprising sterol concentrate, and a heavy condensate flowing down at the heated surface, comprising esters;

In a conventional vacuum distillation column, including thin film evaporator or falling film evaporators, the distance between the heated surface and the condensation surface is much longer than the mean free path of molecules at the operating pressure. This adversely effects the separation yield and at the same time, it imposes heavy loads on the vacuum production. In order to separate compounds of low volatility, the temperature must be increased, which increases the danger of thermal damage of the distillates. However, in a short path distillation column, the path of the vapor molecules to reach the condenser is not obstructed because the condenser is separated from the heated surface or evaporator by a distance which is shorter or slightly longer than the mean free path of the distilling molecules. Normally, the mean free path in a molecular distiller is a few centimeters. However, in order to reach higher distillation rates, the distance between the heated surface and the condensation surface is slightly longer than the mean free path distance. In a commercial molecular distillation column, the operating pressures can be as low as 0.001 mbar. Short path distillation columns having close condensing and heated surfaces are suitable for the present invention. By closeness, it is understood a distance between them shorter than 100 centimeters, preferably between 3 and 50 centimeters. In many aspects, these short path distillation columns operate as a molecular distiller. Falling film short path distillation columns with or without a flat or rotary scraper and centrifugal short path distillation columns are suitable for the present invention. The yield of the two distillation steps is at least 95% in sterols and the purity of the sterol concentrate is approximately 60%.

(3) Dissolving the light condensate of step (2) in a solvent mixture. To this end, said light condensate is fed to a vessel where it is heated until dissolved in a hydrocarbon/aliphatic alcohol/water mixture containing 30–100% by weight of a liquid hydrocarbon solvent; 0–30% by weight of a short chain aliphatic alcohol; and 0–30% by weight of water. The liquid hydrocarbon solvent can be selected from the group consisting of hexane, heptane, cyclohexane, cyclo-heptane, or any mixture of said solvents. The short chain aliphatic alcohol can be selected from the group consisting of methanol, ethanol, propanol or any mixture of said alcohols;

(4) Cooling the dissolution of step (3) so as to form a solid precipitate comprising high purity sterol concentrate and a residual solution or mother liquor;

(5) Separating the mother liquor of step (4) from the precipitate of step (4);

(6) Removing solvent from the mother liquor of step (5), as to form an residue, (7) Mixing the residue of step (6) with the feed of the rectifying column of the first distillation system;

It has been discovered that the sterol content of residue of step (6) is substantially the same or higher than the sterol content of the raw material fed into the first distillation system, a finding which allows for the mixing of said residue with the raw material entering the rectifying column of the first distillation system, without negatively affecting the sterol content of the feed. This recirculation or back feeding of the residue improves the recovery process, which in turn causes that in a continuous process the overall extraction yield can reach up to 98% with product purity greater than 95%.

The second objective of the present invention is to provide a process for obtaining fatty alcohols of high purity, said process comprising the steps of:

(a) Collecting the light overhead condensate from the rectifying column of the first distillation system;

(b) Dissolving the light overhead condensate of step (a) in a mixture of a liquid hydrocarbon solvent and water containing 0–20% of water by weight and 0–100% of the liquid hydrocarbon solvent, where said solvent can be selected from the group consisting of hexane, heptane, octane, isooctane, toluene, xylene, or any mixture of said solvents;
(c) Cooling the dissolution of step (b) so as to form precipitate; and
(d) Separating the precipitate of step (c) comprising a mixture fatty alcohols from 18 to 26 carbon atoms per molecule.

The third objective of the present invention is to provide a process for recovering esters where said process comprises collecting the heavy condensate of the short path distillation column of the second distillation system.

Said heavy condensate comprising esters can be subjected if wished to alkaline hydrolysis, and the resulting soaps and fatty alcohols and sterols can be separated according with techniques known in the state of art, and the mixture of fatty alcohols and sterols can be mixed with the raw material entering the rectifying column of the first distillation system to further improving overall sterol and fatty alcohol yield.

The fourth objective of the present invention is to provide a process for recovering highly pure sterol concentrate with high yield. Said process comprising the steps of:
A. Distilling the raw material in a third distillation system comprising a short path distillation column. To this end, the raw material which is solid at room temperature, is heated until it liquefies and in this is condition it is fed to the short path distillation column comprising a heated surface and an internal condenser close to the heated surface. The temperature of the heated surface is higher or equal than 100° C., preferably lower than 400° C. and the pressure in the column is higher or equal than 0.001 mbar, preferably lower than 25 mbar. Under these operating conditions, the feed of the third distillation system is efficiently fractionated into a light condensate flowing down at the internal condenser, comprising a mixture of sterol concentrate and wax, and a heavy condensate flowing down the heated surface comprising esters.
B. Feeding the light condensate of step (A) to a fourth distillation system comprising a rectifying column, either a packed bed or perforated plate column, a condenser and a reboiler comprising either a thin film evaporator or a falling film evaporator. The pressure on the top of the rectifying column is higher than or equal to 0.1 mbar, preferably lower than 50 mbar, and the reboiler pressure is higher than or equal to 1 mbar, preferably lower than 100 mbar depending on the number of theoretical stages or the number of theoretical equivalent heights of the column. The temperature of the reboiler or the heated surface of the falling film evaporator or the falling film evaporator is higher than or equal to 100° C., preferably lower than 400° C. From said fourth distillation system a distillate denoted light overhead condensate comprising wax, and a heavy bottom condensate or raffinate comprising sterol concentrate are recovered. The overall yield of the two distillation steps is at least 95% in sterols and the purity of the sterol concentrate is approximately 60%.
C. Dissolving the heavy bottom condensate of step (B) from the fourth distillation system in a solvent mixture. To this end, said condensate is fed to a vessel where is heated until dissolving in a hydrocarbon/aliphatic alcohol/water mixture containing 30–100% by weight of a liquid hydrocarbon solvent; 0–30% by weight of a short chain aliphatic alcohol and 0–30% by weight of water. The liquid hydrocarbon solvent can be selected from the group consisting of hexane, heptane, cyclo-hexane, cyclo-heptane, or any mixture of said solvents. The short chain aliphatic alcohol can be selected from the group consisting of methanol, ethanol, propanol or any mixture of said alcohols;
D. Cooling the dissolution of step (C) so as to form a solid precipitate comprising high purity sterol concentrate and a residual solution or mother liquor;
E. Separating the mother liquor of step (D) from the precipitate of step (D);
F. Removing solvents from the mother liquor of step (E), as to form an residue;
G. Mixing the residue from step (F) with the feed of the short path distillation column of the third distillation system;

It has been discovered that the sterol content of residue of step (F) is substantially the same or higher than the sterol content of the raw material fed into the third distillation system, a finding which allow for the mixing of said residue with the raw material entering the short path column of the third distillation system, without negatively affecting the sterol content of the feed. This recirculation or back feeding of the residue improves the recovery process, which in turn causes that in a continuous process the overall extraction yield can reach up to 98% with product purity greater than 95%.

The fifth objective of the present invention is to provide a process for obtaining highly pure fatty alcohols which comprises:
i. Collecting the light overhead condensate from the rectifying column of the fourth distillation system;
ii. Dissolving said light overhead condensate in a mixture of liquid hydrocarbon solvent and water containing 0–20% of water by weight and 0–100% of the liquid hydrocarbon solvent, where said solvent can be selected from the group consisting of hexane, heptane, octane, isooctane, toluene, Ilene, or any mixture of said solvents;
iii. Cooling the dissolution so as to form precipitate; and
iv. Separating the precipitate comprising a mixture of fatty alcohols from 18 to 26 carbon atoms per molecule.

The sixth objective of the present invention is to provide a process for obtaining esters, said process comprising collecting the heavy condensate from the short path distillation of the third distillation system. Said heavy condensate comprising esters can be subjected if wished to alkaline hydrolysis, and the resulting soaps and the fatty alcohols and sterols can be separated according with techniques known in the state of art, and the mixture of fatty alcohols and sterols can be mixed with the feed of the short path distillation column of the third distillation system to further improving overall sterol and fatty alcohol yield.

DESCRIPTION OF THE DRAWINGS

An embodiment of the system for carrying out the first objective of the instant invention is shown schematically in FIG. 1.

The raw material is loaded through line 1 to a melter 2 which feeds via 3 the distillation column 4 consisting of a vacuum rectifying column provided with a reboiler comprising a thin film evaporator. Wax is obtained via line 5. Via line 6 the heavy bottom residue from the evaporator of the distillation column 4 feeds the short path distillation column 7. The heavy residue of the short path distillation or esters is obtained via line 8. Via line 9 the light condensate from the short path distillation column is fed to the mixer 10 along with fresh solvent mixture 11 and recovered solvent from desolventizer 19 is fed to mixer 10 via line 12. Dissolution from mixer 10 is fed to the crystallizer 14 via line 13. Via line 15 the slurry of sterol concentrate and mother liquor is fed to the separation system 16 producing highly pure sterol current 17 and mother liquor current 18 which is fed to disolventization system 19. Melted solids from disolventizer 19 recirculate via line 20 to the melter 2.

Figure 1:
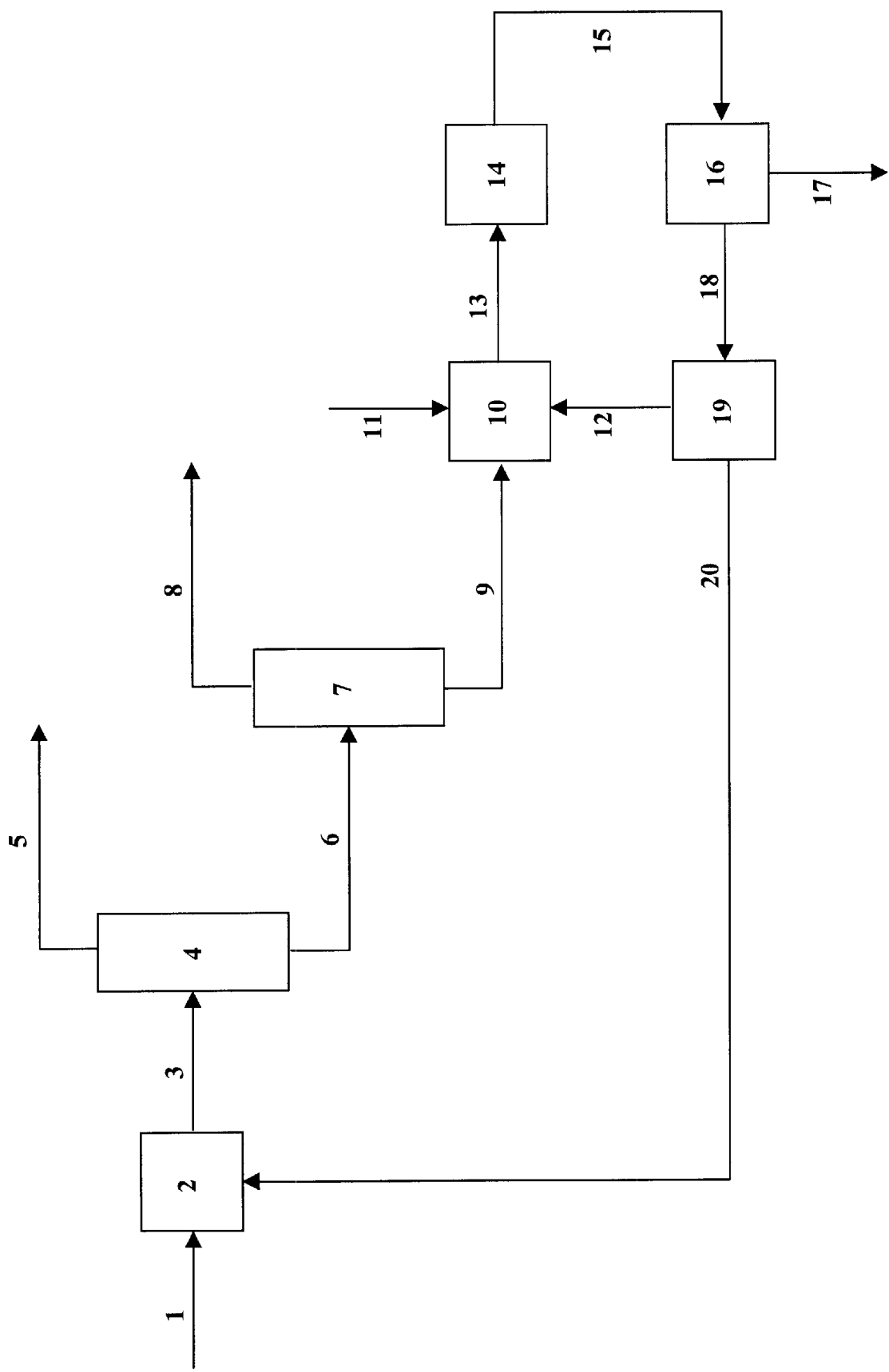
Figure 2:
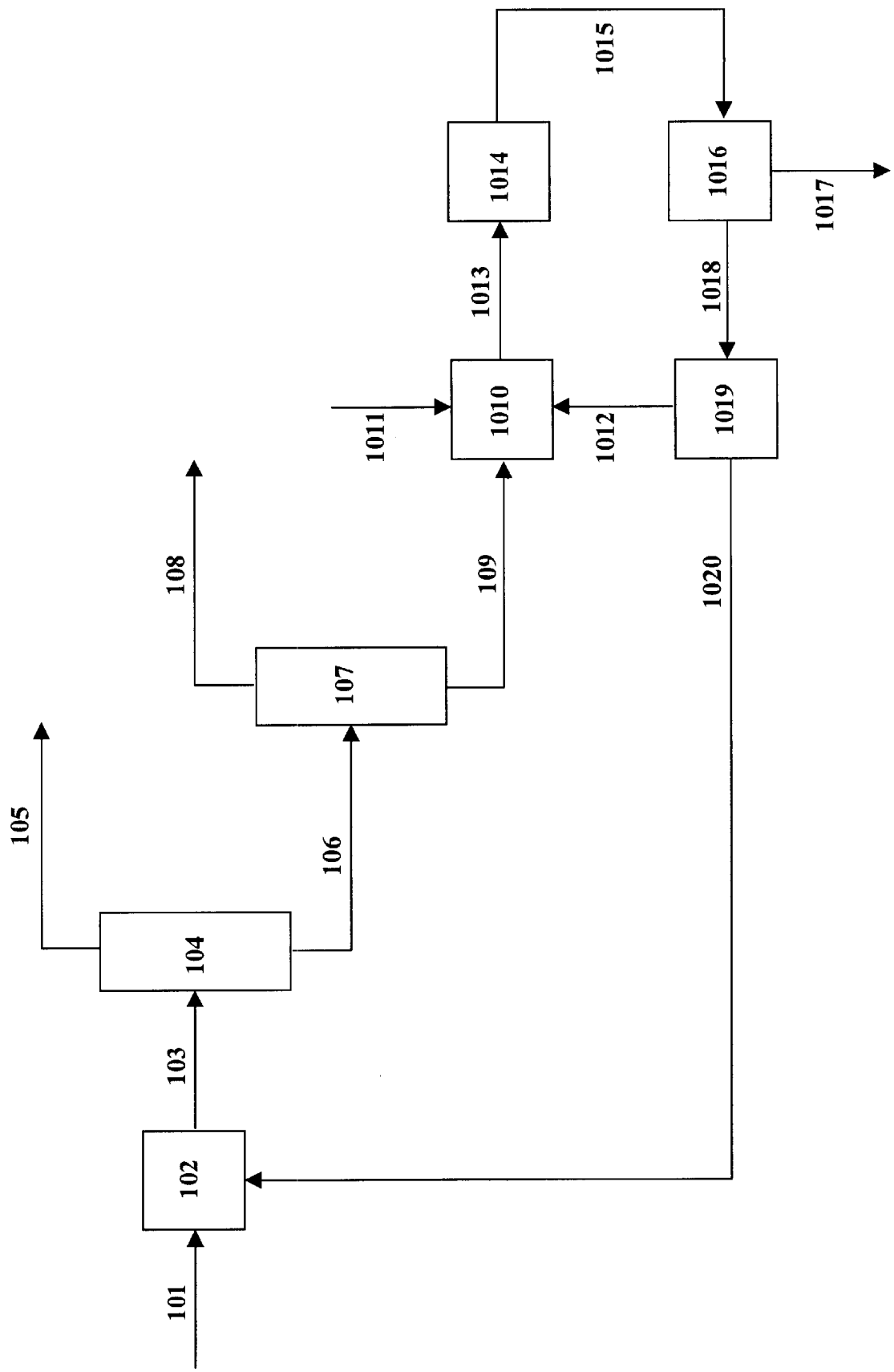

An embodiment of the system for carrying out the fourth objective of the instant invention is shown schematically in FIG. 2.

The raw material is loaded through line 101 to a melter 102 which feeds via line 103 the distillation system 104 comprising a short path distillation column. The heavy residue or esters are obtained via line 105. Via line 106 the light condensate of the short path distillation column 104 feeds the distillation system 107 comprising a vacuum rectifying column provided with a reboiler comprising a thin film evaporator. The light overhead condensate or wax from the distillation system 107 is obtained via line 108. Via line 109 the heavy bottom residue from the distillation system 107 is fed to the mixer 1010 along with a fresh solvent mixture 1011. The solvent mixture recovered from desolventizer 1019 is fed to the mixer 1010 via line 1012. Dissolution from mixer 1010 is fed to the crystallizer 1014 via line 1013. Via line 1015 the slurry of precipitated sterol and mother liquor is fed to separation system 1016 producing highly pure sterol current 1017 and mother liquor current 1018 which is fed to the disolventization system 1019. Melted solids from desolventizer recirculate via line 1020 to the melter 102.

EXAMPLES

Example 1

Mixture of Neutral Matter from Tall Oil Pitch 5000 g of tall oil pitch were mixed with 12.5 kg of a 10% sodium hydroxide solution. The reaction mixture were boiled for one hour and cooled down. Then the reaction mixture were extracted three times with 25 liters of petroleum ether each time, and the ether extracts were desolventized at reduced pressure. 1757 g of neutral matter with a 41.8% of sterols content were obtained.

Example 2

Mixture of Neutral Matter from Black Liquor Soap Skimming 50 kg of black liquor soap with a non-volatile content of 65.3% were used. Mixture of neutral matter were separated by the procedure described in Chilean Patent Application 873/98, obtaining 5870 g of neutral matter with a sterol content of 31.4%.

Example 3

High Purity Sterols in High Yield from Neutral Matter Obtained from Tall Oil Pitch 1750 g of neutral matter of tall oil pitch were fed to a distillation system comprising a packed rectifying column, a thin film reboiler and condenser.

The neutral matter was melted at 50° C. and then heated to 150° C. and fed to the thin film reboiler which whose pressure was 6.8 mbar. Thermal oil at 308° C. was used to heat the thin film reboiler. The top pressure of the rectifying column was 2.9 mbar, the top temperature of the column was 200° C. and the bottom temperature was 220° C. 1195 g of heavy bottom condensate and 555 g of wax or light overhead condensate were obtained.

1152 g of the heavy bottom condensate having 60.1% by weight of sterols were fed to an UIC short path distillation column feeder, model KDL-4. The column evaporation surface were heated with thermal oil at 300° C. and the pressure in the column was 0.4 mbar. This way 994 g of light condensate comprising sterol concentrate with a sterol content of 69.1% and 158 g of heavy condensate comprising esters were obtained.

972 g of the sterol concentrate were dissolved in a mixture of 3400 g of heptane, 150 g of methanol and 150 g of water at 60° C. The solution were cooled to 24° C. and crystals formed were recovered by filtrating the slurry, obtaining 578 g of white crystals with a sterol purity of 95.6% and mother liquor.

The mother liquor were desolventized in a rotavapor at reduced pressure, recovering 394 g of solids with a sterol content of 30.2%.

Sterol purity was 95.6% and the yield was 80.1%.

Next, 390 g of the desolventized filtrate were fed to the thin film evaporator and subjected the procedure described above in the present example. After the crystallization steps, 104 g of white crystals with a sterol purity of 95.7% were obtained. Referring back to the 104 g of sterols obtained from a feed of 1750 g neutral material, an improvement on sterol recovery of 14.6% were obtained without affecting the product purity. In other words, through the process invented, it was possible to achieve an overall sterol recovery yield of 94.7% with a purity higher than 95%.

Example 4

High Purity Sterols in High Yield from Neutral Matter Obtained from Black Liquor Soap Skimmings 3000 g of a mixture of neutral matter produced according with Example 2 were fed to a rectifying column provided with thin film reboiler and condenser. The neutral matter were melted at 50° C. and further heated to 151° C. and fed to the thin film evaporator operated at the pressure of 7.1 mbar and is heated by means of thermal oil at 302° C. The top pressure of the rectifying column was 2.9 mbar, the top temperature of the column was 193° C. and the bottom temperature was 217° C. 1676 g of heavy bottom condensate and 1325 g of light overhead condensate were obtained.

1664 g of the heavy bottom condensate having 55.1% by weight of sterols were fed to an UIC short path distillation column, model KDL-4. The evaporation surface of the column was heated with thermal oil at 300° C. and the column was operated at the pressure of 0.4 mbar. This way 1505 g of light condensate with a sterol content of 60.2% by weight and 159 g of heavy condensate were obtained.

1500 g of the light condensate were dissolved in a mixture 5250 g of heptane, 225 g of methanol and 225 g of water at 60° C. The solution was cooled to 24° C and the crystals formed were recovered by filtrating the slurry obtaining 795 g of white crystals with a sterol content of 96.4%.

The filtrate or mother liquor were desolventized in a rotavapor at reduced pressure recovering 705 g of solids with a sterol content of 19.6%.

Sterol purity was 96.2% and the yield was 88.2%.

Next, 800 g of a mixture of neutral matter produced according Example 2 were mixed with 700 g of the desolventized filtrate. After subjecting the mixture to the process described in the present example 346 g of white crystals with a sterol purity of 96.0% were obtained.

The overall efficiency in this example corresponds (3800 g of neutral matter leading to 1149 g of sterol crystals) to 92.7% with a purity of 96%.

Example 5

Unsaponifiable Material from Esters 30 g of heavy condensate from Example 3 were mixed with 100 ml 15% of sodium hydroxide in a Parr 6890 reactor at the temperature of 175° C. and left to react during 30 minutes. The saponified mixture were cooled to room temperature and the unsaponified material was extracted with petroleum ether. The ether phase was desolventized, recovering 22.2 g of unsaponified material with a sterol content of 43.2%.

Example 6

Fatty Alcohols from Wax 100 g of light overhead condensate from Example 4 were mixed with 450 g of heptane and 30 g of water at 50° C. The mixture were cooled to 0° C. and the precipitate formed were recovered by filtrating the slurry, thus obtaining 23.5 g of white crystals with a fatty alcohol content of 98.2% and a relative composition shown in Table 1.

TABLE 1

Relative composition of fatty alcohols

| Fatty alcohol | Relative percentage |
| --- | --- |
| Eicosanol | 9.2 |
| Heneicosanol | 0.8 |
| Docosanol | 56.4 |
| Tricosanol | 1.9 |
| Tetracosanol | 30.6 |
| Pentacosanol | 0.3 |
| Hexacosanol | 1.6 |

Modifications to the present invention can be made by those who are experts in the state of the art. Therefore, the present invention is not necessarily limited to the described examples of systems and processes.

What is claimed is:

1. A continuous process for the recovery of sterols from mixtures of neutral matter obtained from black liquor soap skimmings or tall oil pitch, comprising the steps of:

(a) feeding the mixture of neutral matter to a first distillation system where said distillation system comprises: a rectifying column, condenser and thin film reboiler so as to form a first fraction comprising long chain aliphatic alcohols and a second fraction comprising sterols and esters;

(b) recovering said first and second fractions;

(c) feeding said second fraction to a second distillation system comprising a short path distillation column so as to form a third fraction comprising sterols and a fourth fraction comprising esters;

(d) recovering said third and fourth fractions;

(e) dissolving said third fraction so as to form a solution in a mixture comprising a liquid hydrocarbon solvent, short chain aliphatic alcohol and water;

(f) cooling the solution of step (e) so as to form a precipitate;

(g) separating the precipitate formed in step (f) from the mother liquor;

(h) evaporating the mother liquor of step (g) so as to form a residue; and (i) mixing the residue of step (h) with the mixture of neutral matter of step (a).

2. The process according to claim 1, wherein the rectifying column comprises a packed bed column, a falling film reboiler and a condenser or a perforated plate column, a falling film reboiler and a condenser.

3. The process according to claim 2, wherein the pressure in the column is within the range from about 0.1 mbar to about 50 mbar and the temperature in the reboiler is within the range from about 100° C. to about 400° C.

4. The process according to claim 1, wherein the pressure in the short path distillation column is within the range of about 0.001 mbar to about 25 mbar and the temperature of the evaporation surface in said column is within the range of about 100° C. to about 400° C.

5. The process according to claim 1 comprising the steps of:

dissolving the first fraction of the first distillation system in a mixture containing
0–20% by weight of water
0–100% by weight of a solvent selected from group consisting of hexane, heptane, octane, isooctane, toluene, xilene or mixtures of two or more of these solvents;

cooling the solution of step so as to form a precipitate and mother liquor;

separating the precipitate from the mother liquor so as to form a mixture of long chain aliphatic alcohols comprising 18 to 26 carbon atoms per molecule.

6. The process according to claim 1, wherein the mixture of solvents of step (e) contains 30–100% by weight of a liquid hydrocarbon solvent selected from the group consisting of hexane, heptane, cyclo-hexane, cyclo-heptane or mixtures of two o more of said liquid hydrocarbon solvent;

0–30% by weight of a short chain aliphatic alcohol selected from the group consisting of methanol, ethanol, propanol or a mixture of two or more of said alcohols;

0–30% by weight of water.

7. The process according to claim 6, comprising the steps of:

A. cooling the solution so as to form a precipitate;

B. separating the precipitate of step (A) from the mother liquor; and

C. desolventizing the precipitate of step (B) so as to form a dry precipitate comprising at least 90% in weight of sterols.

8. A process for the recovery of sterols from mixtures of neutral matter obtained from of black liquor soap skimmings or from tall oil pitch, comprising the steps of:

(j) feeding the mixture of neutral matter to a distillation system where said distillation system comprises a short path distillation column so as to form a first fraction comprising long chain aliphatic alcohols and sterols, a second fraction comprising esters;

(k) recovering said first and second fractions;

(l) feeding said first fraction to another distillation system comprising a rectifying column, condenser and reboiler so as to form a third fraction comprising long chain aliphatic alcohols, and a fourth fraction comprising sterols;

(m) recovering said third and fourth fractions;

(n) dissolving said fourth fraction so as to form a solution in a mixture comprising a liquid hydrocarbon solvent, short chain aliphatic alcohol and water;

(o) cooling the solution of step (n) so as to form a precipitate and mother liquor;

(p) separating the precipitate formed in step (o) from the mother liquor;

(q) evaporating the mother liquor of step (p) so as to form a residue; and (r) mixing the residue of step (q) with the mixture of neutral matter of step (j).

9. The process according to claim 8, wherein the rectifying column comprises a packed bed column, a falling film reboiler and a condenser or a perforated plate column, a falling film reboiler and a condenser.

10. The process according to claim 8, wherein the pressure in the short path distillation column is within the range of about 0.001 mbar to about 25 mbar and the temperature of the evaporation surface in said column is within the range of about 100° C. to about 400° C.

11. The process according to claim 8, wherein the pressure in the rectifying column is within the range from about 0.1 mbar to about 50 mbar and the temperature in the reboiler is within the range from about 100° C. to about 400° C.

12. The process according to claim 9, wherein the pressure in the rectifying column is within the range from about 0.1 mbar to about 50 mbar and the temperature in the reboiler is within the range from about 100° C. to about 400° C.

13. The process according to claim 8 comprising the steps of;

dissolving the third fraction of the fourth distillation system in a mixture so as to form a solution, said mixture containing 0–20% by weight of water 0–100% by weight of a solvent selected from group consisting of hexane, heptane, octane, isooctane, toluene, xilene or mixtures of two or more of these solvents; cooling the solution so as to from a precipitate and mother liquor;

separating the precipitate from the mother liquor so as to form a mixture of long chain aliphatic alcohols comprising 18 to 26 carbon atoms per molecule.

14. The process according to claim 8, wherein the mixture of solvents of step (n) contains 30–100% by weight of a liquid hydrocarbon solvent selected from the group consisting of hexane, heptane, cyclo-hexane, cyclo-heptane or mixtures of two o more of said liquid hydrocarbon solvent 0–30% by weight of a short chain aliphatic alcohol selected from the group consisting of methanol, ethanol, propanol or a mixture of two or more of said alcohols 0–30% by weight of water.

15. The process according to claim 8, comprising the steps of:

(s) cooling the solution so as to form a precipitate and mother liquor;

(t) separating the precipitate of step (s) from the mother liquor; and (u) desolventizing the separated precipitate of step (t) as to form a dry precipitate comprising at least 90% in weight of sterols.

16. The process according to claim 1, comprising the steps of:

saponifying the fourth fraction of step (d) so as to form a mixture of soaps and unsaponifiable materials;

separating the mixture of soaps and unsaponified materials;

recovering the unsaponified materials;

mixing the unsaponified material with the mixture of neutral matter of step (a) or of step (j).

17. The process according to claim 8, comprising the steps of:

saponifying the second fraction of step (k) so as to form a mixture of soaps and unsaponifiable materials;

separating the mixture of soaps and unsaponified materials;

recovering the unsaponified materials;

mixing the unsaponified material with mixture of neutral matter of step (j) or step (a).

* * * * *